United States Patent
Koren et al.

(10) Patent No.: US 6,312,376 B1
(45) Date of Patent: *Nov. 6, 2001

(54) APPARATUS FOR GENERATING ELECTROMAGNETIC WAVEFORMS

(76) Inventors: Stanley A. Koren, 262 Nepahwin Ave., Sudbury, Ontario (CA), P3E 2H6; Michael A. Persinger, 261 Wilson Street, Sudbury, Ontario (CA), P3E 2S3

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/141,752

(22) Filed: Aug. 28, 1998

(30) Foreign Application Priority Data

Aug. 29, 1997 (CA) .................................................. 2214296

(51) Int. Cl.[7] .................................................. A61N 2/04
(52) U.S. Cl. .................................................. 600/13
(58) Field of Search .................... 600/300, 301, 600/544, 545, 9, 13, 14, 15; 128/897, 898; 607/59

(56) References Cited

U.S. PATENT DOCUMENTS

| 4,315,503 | * | 2/1982 | Ryaby et al. | 128/1.5 |
|---|---|---|---|---|
| 5,169,380 | * | 12/1992 | Brennan | 600/26 |
| 5,330,410 | * | 7/1994 | Baylink | 600/13 |
| 5,453,072 | * | 9/1995 | Anninos et al. | 600/9 |
| 5,634,939 | * | 6/1997 | Kuster et al. | 607/59 |
| 5,769,778 | * | 6/1998 | Abrams et al. | 600/14 |

* cited by examiner

Primary Examiner—John P. Lacyk
Assistant Examiner—Joseph A. Cadugan
(74) Attorney, Agent, or Firm—Katten Muchin Zavis

(57) ABSTRACT

An apparatus for generating electromagnetic waveforms to stimulate a subject includes an electromagnetic waveform signal generator to generate analog signals representing desired electromagnetic waveforms. A selector responsive to channel select input applies the analog signals to selected output channels of the selector. Electromagnetic devices are coupled to the output channels of the selector to convert analog signals into electromagnetic waveforms. The electromagnetic devices coupled to the selected output channels are driven by the analog signals to expose a subject wearing the electromagnetic devices to the desired electromagnetic waveforms.

34 Claims, 2 Drawing Sheets

| BINARY | DECIMAL | DAC OUTPUT (VOLTS) |
|---|---|---|
| 11111111 | 255 | 6 |
| 01111111 | 127 | 0 |
| 00000000 | 0 | -6 |

APPARATUS FOR GENERATING ELECTROMAGNETIC WAVEFORMS

FIELD OF THE INVENTION

The present invention relates to neuropsychology and in particular to a method and apparatus for generating electromagnetic waveforms to stimulate a subject.

BACKGROUND OF THE INVENTION

Diverse studies have shown that the behavioral, cellular and physiological functions of animals can be affected by magnetic stimuli. Weak magnetic fields exert a variety of biological effects ranging from alterations in cellular ion flux to modifications of animal orientation and learning, and therapeutic actions in humans.

There are several theories addressing the mechanism of the effect that magnetic field exposure has on tissues. For example, low frequency magnetic field exposures have been proposed to exert their effect(s) through induction of electric currents. Although not widely believed, it has also been proposed that weak magnetic fields are detected by particles of magnetite in tissue and by virtue of this detection have a physiological effect.

Although the mechanism of the effects of magnetic field exposure on tissues is uncertain, it is clear that magnetic fields are a physical agent which have little attenuation in tissue and therefore, can be used to alter endogenous processes provided the magnetic fields can be detected and their detection coupled to a physiological process. In view of this, it is desired to expose subjects to magnetic fields to treat physiological, neurological and behavioral disorders and to determine the effect of a variety of magnetic stimuli on subjects.

It is therefore an object of the present invention to provide a novel method and apparatus for generating electromagnetic waveforms to stimulate a subject.

SUMMARY OF THE INVENTION

According to one aspect of the present invention there is provided an apparatus for generating electromagnetic waveforms to stimulate a subject. The apparatus includes an electromagnetic signal generator generating analog signals corresponding to electromagnetic waveforms. A selector is responsive to channel select input and applies the analog signals output by the electromagnetic signal generator onto selected output channels thereof. Electromagnetic devices are coupled to the output channels of the selector and convert the analog signals into electromagnetic waveforms to expose a subject wearing the electromagnetic devices to the electromagnetic waveforms.

Preferably, the electromagnetic waveform signal generator is programmable. In a preferred embodiment, the electromagnetic waveform signal generator includes a processing unit to generate digital representations of the desired electromagnetic waveforms and an analog to digital converter coupled to the processing unit to convert the digital representations into corresponding analog signals. The processing unit preferably is coupled to the selector and provides the channel select input.

Preferably the processing unit is programmable to set a desired delay between successive digital samples of the digital representations output by the processing unit. It is also preferred that the processing unit is programmable to set a sequence of selected output channels on which the analog signals are to be applied. The processing unit is programmable to repeat the sequence a desired number of times, to set the duration the analog signals are output on each selected output channel in the sequence, to set a desired delay between repetition of the sequence, and to set a desired acceleration sequence. The acceleration sequence determines a change in the duration the analog signals are applied to each successive selected output channel in the sequence.

Preferably, the electromagnetic devices are arranged in pairs with each pair being coupled to a respective output channel of the selector. The electromagnetic devices are attached to head wear to be worn by the subject and are in the form of solenoid assemblies. Selected pairs of the solenoid assemblies are in phase and selected other pairs of the solenoid assemblies are out of phase.

According to another aspect of the present invention there is provided an apparatus for generating electromagnetic waveforms to stimulate a subject that comprises a processing unit having memory storing at least one digital representation of a desired electromagnetic waveform. A digital analog to converter is coupled to the processing unit to convert digital representations of electromagnetic waveforms received from the processing unit into corresponding analog signals. A selector is responsive to channel select input from the processing unit to apply the analog signals onto selected output channels of the selector. Electromagnetic devices are coupled to the output channels of the selector to convert analog signals into electromagnetic waveforms. The electromagnetic devices that are coupled to the selected output channels are driven by the analog signals to expose a subject wearing the electromagnetic devices to the electromagnetic waveforms. The processing unit is programmable to expose the subject to a desired sequence of tailored electromagnetic waveforms to provide a desired stimulus to the subject.

BRIEF DESCRIPTION OF THE DRAWINGS

An embodiment of the present invention will now be described more fully with reference to the accompanying drawings in which:

FIG. 2b is an illustration of an analog conversion of the digital representation of FIG. 2a; and FIG. 3 is a table showing a digital to analog conversion of points along a digital representation of an electromagnetic waveform.

DETAILED DESCRIPTION OF THE PREFERRED EMBODIMENTS

Figure 1:
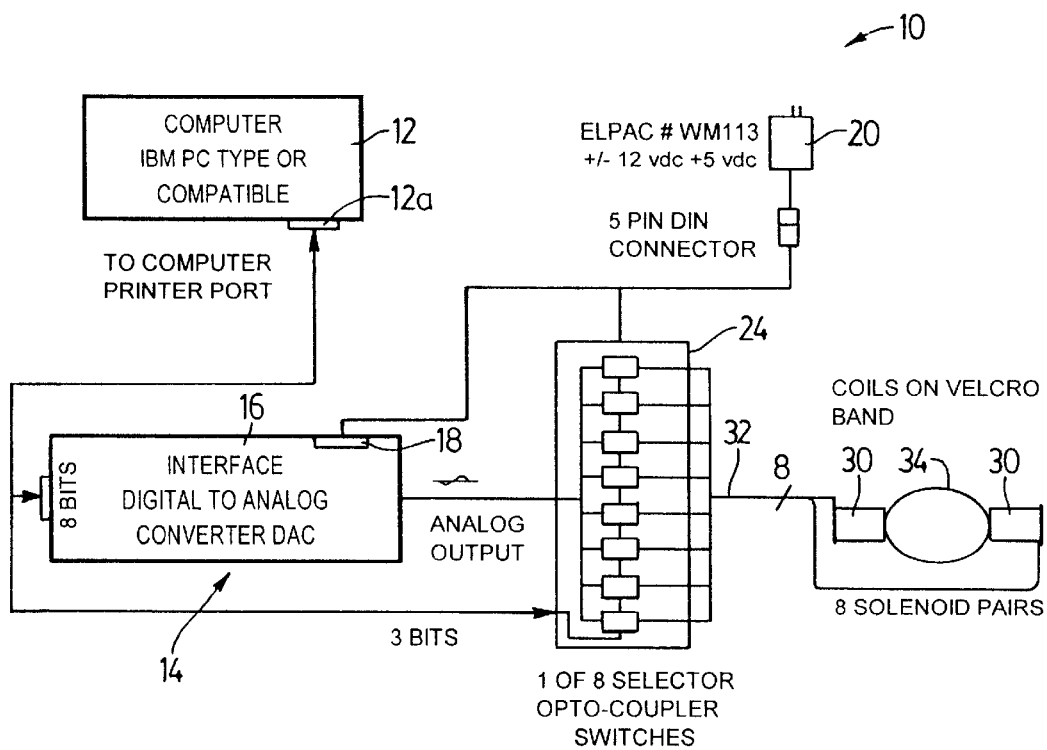
FIG. 1 is a schematic diagram of an apparatus for generating electromagnetic waveforms in accordance with the present invention.

Referring now to FIG. 1, an apparatus for generating electromagnetic waveforms to which a subject is to be exposed is shown and is generally indicated to by reference numeral 10. As can be seen, apparatus 10 includes a processing unit in the form of a personal computer 12. Connected to a parallel port 12a of the personal computer 12 is an interface 14 including an 8-bit digital to analog converter 16 such as that manufactured by National Semiconductor under part No. DAC0800LCN, and a two-stage direct coupled operational amplifier circuit 18 utilizing LM741CN operational amplifiers. Operational amplifier circuit 18 is powered by an ELPAC WM113 DC power supply (+5 v@860 ma;+/−12 v@300 ma) 20.

The output of the digital to analog converter 16 is conveyed to a one-of eight channel selector 24 including a plurality opto-couplers. Selector 24 is also powered by power supply 20 and is responsive to input received from the parallel port 12a of personal computer 12 to enable output channels of the selector 24 on which the output of digital to analog converter 16 is to be applied.

Each output channel of the selector 24 is electrically coupled to a pair of solenoid assemblies 30 (only one pair of which is shown) in parallel, by a shielded cable 32. The connections between the selector output channels and the solenoid assemblies are such that some of the pairs of solenoid assemblies 30 are in phase (i.e. the solenoid assemblies are connected in North to North magnetic polarity) and some of the pairs of solenoid assemblies 30 are out of phase (i.e. the solenoid assemblies are connected in North to South magnetic polarity). The solenoid assemblies 30 of each pair are attached to a headband 34 to be worn by a subject and are positioned on the headband so that the solenoid assemblies of each pair are diametrically opposed. Adjacent solenoid assemblies 30 are separated by a distance equal to approximately 0.8 inches.

Each solenoid assembly 30 includes a solenoid constructed from a reed relay (Intertan 275–232) with the reed switch removed and replaced by a steel nail core. The solenoids are housed within casings attached to the headband 34 by way of hook and loop fabric.

Figure 2A:
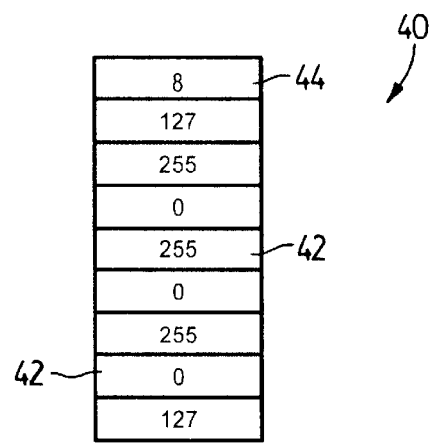
FIG. 2a is a table of points along a digital representation of an electromagnetic waveform.
Figures 2B, 3:
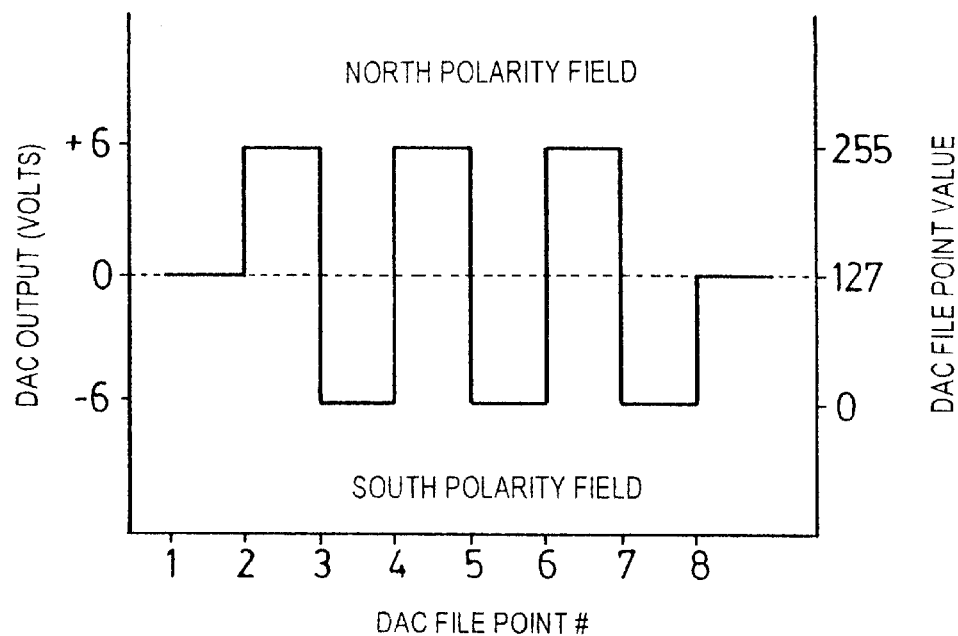

The electromagnetic waveforms to which subjects are to be exposed are digitally stored in the personal computer 12 as DAC (see FIG. 2a) files 40 and can be derived from mathematical equations, spoken words or custom designed. Each DAC file 40 includes a list of individual points 42 representing points along the corresponding electromagnetic waveform together with a header 44 indicating the number of individual points that are stored in the DAC file. The DAC file is either in the form of a DOS-text or ASCII-text file with one individual point entry per line. Each individual point has a value in the range of 0 to 255 represented as an 8-bit binary number. FIGS. 2a and 2b illustrate an example of a DAC file 40 that is a digital representation of an electromagnetic square waveform and its analog equivalent. As can be seen, the DAC file header 44 indicates that eight individual points 42 are in the DAC file 40.

The value assigned to each individual point in a DAC file corresponds to an analog output voltage. FIG. 3 shows the conversion of individual point values to analog voltage levels. As can be seen, value 255 (binary "11111111") corresponds to an analog voltage equal to 6 volts, value 127 (binary "01111111") corresponds to an analog voltage equal to 0 volts, and a value 0 (binary "00000000") corresponds to an analog voltage equal to −6 volts.

Stored within the personal computer 12 is a computer program which when executed, outputs DAC files 40 to the digital to analog converter 16 and enables selected channels of the selector 24 to drive selected pairs of the solenoid assemblies 30 thereby exposing the subject to electromagnetic waveforms. The computer program allows a user to:

(i) select the form of the electromagnetic waveforms to be generated by creating DAC files;
(ii) determine the delay between each individual point of an electromagnetic waveform being generated (i.e. set the frequency of the electromagnetic waveform);
(iii) determine the number of times the electromagnetic waveform is to be repeated;
(iv) determine the delay between each repeat of the electromagnetic waveform;
(v) determine the channel sequence on which the electromagnetic waveform is to be output (i.e. sequence limit);
(vi) determine the duration the electromagnetic waveform is to be applied to each channel (i.e. sequence interval); and
(vii) determine a sequence acceleration for the repeated electromagnetic waveform.

For example, if the sequence limit is set equal to four, the sequence acceleration is set equal to −2 msecs, the sequence interval is set equal to 10 msecs, and a DAC file 40 is selected to be repeated three times, the electromagnetic waveform would firstly be presented on channel 1 for 10 msecs, then on channel 2 for 8 msecs, and then on channel 3 for 6 msecs and then lastly on channel 4 for 4 msecs. After that the above sequence would be repeated until the sequence had been output a total of four times.

In use, an operator creates DAC files 40 representing the desired electromagnetic waveforms to which a subject is to be exposed. Once the operator has created the DAC files, the operator assigns values to the above described parameters.

Once the parameters have been assigned values, the headband 34 is placed on the head of a subject. The computer program is then executed by the personal computer 12 causing the computer program to select the DAC file 40 to be processed and causes the personal computer to output the individual points with the set delay between individual points as 8-bit binary values to the digital to analog converter 16 via the parallel port 12a. The personal computer 12 also outputs 3-bit values representing the channel sequence via the parallel port 12a that are conveyed to the selector 24. The selector 24 in turn enables the desired channels.

As the digital to analog converter 16 receives the output 8-bit binary values, it converts the binary values to corresponding analog signals and supplies the analog signals to the selector 24. The selector in turn passes the analog signals onto its enabled output channels.

As the analog signals appear on the channels, the selector output solenoid assemblies 30 are driven to expose the subject wearing the headband to the desired electromagnetic waveforms. By using parameter passing and batch processing, the subject can be exposed to a series of different electromagnetic waveforms for different durations and on different channels.

Although a preferred embodiment of the present invention has been described, those of skill in the art will appreciate that variations and modifications may be made without departing from the spirit and scope thereof as defined by the appended claims.

We claim:
1. An apparatus for generating electromagnetic waveforms to stimulate a subject comprising:
an electromagnetic waveform signal generator including memory storing at least one digital dual polarity electromagnetic waveform definition file, said at least one definition file including a number of points representing points along an electromagnetic waveform to be generated, said electromagnetic waveform signal generator being programmable to allow said at least one definition file to be custom tailored on a point-by-point basis and being operable to output analog signals corresponding to the points in said at least one definition file at a precise rate in accordance with user selected parameters;
a selector responsive to channel select input to apply said analog signals to selected output channels of said selector, said electromagnetic waveform generator gen- erating said channel select input so that said analog signals are applied to multiple selected output channels following a precise timing schedule in accordance with user selected parameters; and electromagnetic devices coupled to the output channels of said selector to convert analog signals into electromagnetic waveforms, the electromagnetic devices coupled to said selected output channels being driven by said analog signals thereby to expose a subject wearing said electromagnetic devices to electromagnetic waveform.

2. An apparatus as defined in claim 1 wherein said electromagnetic devices are arranged in pairs, each pair of electromagnetic devices being coupled to a respective output channel of said selector.

3. An apparatus as defined in claim 2 wherein said electromagnetic devices are attached to head wear to be worn by said subject.

4. An apparatus as defined in claim 3 wherein said electromagnetic devices are in the form of solenoid assemblies.

5. An apparatus as defined in claim 4 wherein selected pairs of said solenoid assemblies are in phase and selected other pairs of said solenoid assemblies are out of phase.

6. An apparatus as defined in claim 1 wherein said custom tailored digital electromagnetic waveforms are derived from mathematical equations or spoken word equivalencies.

7. An apparatus as defined in claim 6 wherein said electromagnetic waveform generator includes a processing unit including said memory, said memory storing a plurality of custom tailored dual polarity digital electromagnetic waveform definition files, said electromagnetic waveform generator further including a digital to analog converter coupled to said processing unit to convert the points in said definition files that are output by said processing unit into corresponding analog signals.

8. An apparatus as defined in claim 7 wherein said processing unit is coupled to said selector and provides said channel select input.

9. An apparatus is defined in claim 8 wherein said processing unit is programmable to set a desired delay between successive points output by said processing unit.

10. An apparatus as defined in claim 9 wherein said processing unit is programmable to set a sequence of selected output channels on which said analog signals are to be applied.

11. An apparatus as defined in claim 10 wherein said processing unit is programmable to repeat said output channel sequence a desired number of times.

12. An apparatus as defined in claim 11 wherein said processing unit is programmable to set a desired delay between repetition of said output channel sequence.

13. An apparatus as defined in claim 10 wherein said processing unit is programmable to set the duration said analog signals are output on each selected output channel in said output channel sequence.

14. An apparatus as defined in claim 13 wherein said processing unit is programmable to set a desired acceleration sequence, said acceleration sequence determining a change in the duration said analog signals are applied to each successive selected output channel in said output channel sequence.

15. An apparatus for generating electromagnetic waveforms to stimulate a subject comprising:

a processing unit having memory storing a plurality of digital dual polarity electromagnetic waveform definition files, each definition file including a number of points representing an electromagnetic waveform to be generated;

a digital to analog converter coupled to said processing unit and converting digital points received from said processing unit into corresponding analog signals;

a selector responsive to channel select input from said processing unit and applying said analog signals onto selected output channels of said selector; and electromagnetic devices coupled to the output channels of said selector and converting analog signals into electromagnetic waveforms, the electromagnetic devices coupled to said selected output channels being driven by said analog signals thereby to expose a subject wearing said electromagnetic devices to said electromagnetic waveforms, wherein said processing unit is programmable to allow each of said definition files to be custom tailored on a point-by-point basis and to output definition files in a sequence at a precise rate in accordance with user selected parameters and wherein said processing unit is responsive to user selected parameters so that said analog signals are applied to multiple selected output channels following a precise timing schedule to provide a desired stimulus to said subject.

16. An apparatus as defined in claim 15 wherein said processing unit is programmable to set a desired delay between successive digital points output by said processing unit.

17. An apparatus as defined in claim 16 wherein said processing unit is programmable to repeat output of said desired sequence a desired number of times.

18. An apparatus as defined in claim 17 wherein said processing unit is programmable to set the duration said analog signals are output on each selected output channel in said sequence.

19. An apparatus as defined in claim 18 wherein said processing unit is programmable to set a desired delay between repetition of said sequence.

20. An apparatus as defined in claim 19 wherein said processing unit is programmable to set a desired acceleration sequence, said acceleration sequence determining a change in the duration said analog signals are applied to each successive selected output channel in said sequence.

21. An apparatus as defined in claim 15 wherein said electromagnetic devices are arranged in pairs, each pair of electromagnetic devices being coupled to a respective output channel of said selector.

22. An apparatus as defined in claim 21 wherein said electromagnetic devices are attached to head wear to be worn by said subject.

23. An apparatus as defined in claim 22 wherein said electromagnetic devices are in the form of solenoid assemblies.

24. An apparatus as defined in claim 23 wherein selected pairs of said solenoid assemblies are in phase and selected other pairs of said solenoid assemblies are out of phase.

25. An apparatus as defined in claim 15 wherein said custom tailored digital electromagnetic waveforms are derived from mathematical equations or spoken word equivalencies.

26. An apparatus for generating electromagnetic waveforms to stimulate a subject comprising:

an electromagnetic waveform signal generator to generate analog signals corresponding to electromagnetic waveforms;

a selector responsive to channel select input to apply said analog signals to selected output channels of said selector; and electromagnetic devices in the form of solenoid assemblies coupled to the output channels of said selector and converting analog signals into electromagnetic waveforms to expose a subject wearing said electromagnetic devices to said electromagnetic waveforms, said solenoid assemblies being arranged in pairs, each pair of solenoid assemblies being coupled to a respective output channel of said selector, selected pairs of said solenoid assemblies being in phase and selected other pairs of said solenoid assemblies being out of phase.

27. An apparatus as defined in claim 26 wherein said solenoid assemblies are attached to head wear to be worn on the head of a subject.

28. An apparatus as defined in claim 27 wherein the solenoid assemblies of each pair are diametrically opposed.

29. An apparatus for generating electromagnetic waveforms to stimulate a subject comprising:

an electromagnetic waveform signal generator having a processing unit including memory storing digital representations of electromagnetic waveforms in dual polarity and a digital to analog converter converting said digital representations into corresponding analog signals;

a selector responsive to channel select input received from said processing unit and applying said analog signals onto selected output channels of said selector; and electromagnetic devices coupled to the output channels of said selector and converting analog signals into electromagnetic waveforms to expose a subject wearing said electromagnetic devices to said electromagnetic waveforms, wherein said processing unit is programmable to set a sequence of selected output channels onto which said analog signals are applied and to set an acceleration sequence, said acceleration sequence determining a change in the duration said analog signals are applied onto each selected output channel in said output channel sequence.

30. An apparatus as defined in claim 29 wherein said processing unit is further programmable to set the duration said analog signals are applied onto each selected output channel in said output channel sequence.

31. An apparatus as defined in claim 30 wherein said processing unit is further programmable to set a delay between successive digital samples of said electromagnetic waveforms output to said digital to analog converter.

32. An apparatus as defined in claim 31 wherein said processing unit is further programmable to repeat said output channel sequence a desired number of times.

33. An apparatus for generating electromagnetic waveforms to stimulate a subject comprising:

a processing unit having memory storing a plurality of digital representations of electromagnetic waveforms;

a digital to analog converter coupled to said processing unit and converting digital representations received from said processing unit into corresponding analog signals;

a selector responsive to channel select input from said processing unit and applying said analog signals onto selected output channels of said selector; and electromagnetic devices coupled to the output channels of said selector and converting analog signals into electromagnetic waveforms, the electromagnetic devices coupled to said selected output channels being driven by said analog signals to expose a subject wearing said electromagnetic devices to said electromagnetic waveforms, wherein said processing unit is programmable to:

set an output channel sequence of selected output channels onto which said analog signals are applied;

set an acceleration sequence, said acceleration sequence determining a change in the duration said analog signals are applied onto each selected output channel in said output channel sequence;

set the duration said analog signals are applied onto each selected output channel in said output channel sequence;

repeat said output channel sequence a desired number of times; and set a desired delay between repetitions of said output channel sequence.

34. An apparatus as defined in claim 33 wherein said processing unit is further programmable to set a delay between successive digital samples of said digital electromagnetic waveforms output to said digital to analog converter.

* * * * *